(12) United States Patent
Hodgkinson et al.

(10) Patent No.: US 9,362,571 B2
(45) Date of Patent: *Jun. 7, 2016

(54) DEGRADABLE IMPLANTABLE BATTERY

(71) Applicant: Covidien LP, Mansfield, MA (US)

(72) Inventors: Gerald Hodgkinson, Guilford, CT (US); William O. Powers, Cheshire, CT (US); Ahmad Robert Hadba, Fort Worth, TX (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/603,750

(22) Filed: Jan. 23, 2015

(65) Prior Publication Data

US 2015/0140387 A1 May 21, 2015

Related U.S. Application Data

(63) Continuation of application No. 14/077,397, filed on Nov. 12, 2013, now Pat. No. 8,968,927, which is a continuation-in-part of application No. 13/183,708, filed on Jul. 15, 2011, now Pat. No. 8,968,926.

(51) Int. Cl.
*A61N 1/00* (2006.01)
*H01M 6/34* (2006.01)
*A61N 1/378* (2006.01)
(Continued)

(52) U.S. Cl.
CPC ............. *H01M 6/34* (2013.01); *A61B 5/6846* (2013.01); *A61N 1/378* (2013.01); *A61N 1/3787* (2013.01); *H01M 4/131* (2013.01); *H01M 4/134* (2013.01); *H01M 4/137* (2013.01); *H01M 4/38* (2013.01); *H01M 4/42* (2013.01); *H01M 4/466* (2013.01); *H01M 4/485* (2013.01); *H01M 4/602* (2013.01);
(Continued)

(58) Field of Classification Search
CPC ......... H01M 6/34; H01M 4/602; H01M 4/38; H01M 4/466; H01M 4/42; H01M 4/485; A61B 5/6846; A61N 1/3787
See application file for complete search history.

(56) References Cited

U.S. PATENT DOCUMENTS 6,184,266 B1 2/2001 Ronan et al.
6,368,356 B1 4/2002 Zhong et al.
(Continued)

FOREIGN PATENT DOCUMENTS

WO 98/02204 A1 1/1998
WO 2008052136 A2 5/2008
(Continued)

OTHER PUBLICATIONS

European Search Report corresponding to EP 14 19 2615.4, completed Mar. 19, 2015 and mailed Apr. 1, 2015; (7 pp).

*Primary Examiner* — Ula C Ruddock
*Assistant Examiner* — Lisa S Park

(57) ABSTRACT

A biodegradable battery is provided. The battery includes an anode comprising a material including an inner surface and an outer surface, wherein electrochemical oxidation of the anode material results in the formation of a reaction product that is substantially non-toxic and a cathode comprising a material including an inner surface and an outer surface, the inner surface of the cathode being in direct physical contact with the inner surface of the anode, wherein electrochemical reduction of the cathode material results in the formation of a reaction product that is substantially non-toxic, and wherein the cathode material presents a larger standard reduction potential than the anode material.

11 Claims, 4 Drawing Sheets

(51) Int. Cl.
*H01M 6/02* (2006.01)
*H01M 4/131* (2010.01)
*H01M 4/134* (2010.01)
*H01M 4/137* (2010.01)
*H01M 4/62* (2006.01)
*H01M 6/04* (2006.01)
*A61B 5/00* (2006.01)
*H01M 4/38* (2006.01)
*H01M 4/42* (2006.01)
*H01M 4/46* (2006.01)
*H01M 4/485* (2010.01)
*H01M 4/60* (2006.01)

(52) U.S. Cl.
CPC ............... *H01M 4/622* (2013.01); *H01M 6/02* (2013.01); *H01M 6/04* (2013.01); *Y02E 60/122* (2013.01)

(56) References Cited

U.S. PATENT DOCUMENTS

| | | | |
|---|---|---|---|
| 7,605,232 B2 | 10/2009 | Pathak | |
| 8,968,927 B2 | 3/2015 | Hodgkinson et al. | |
| 2003/0023190 A1 | 1/2003 | Cox | |
| 2003/0129214 A1* | 7/2003 | Bornstein | A61L 27/34 424/423 |
| 2010/0055570 A1 | 3/2010 | Rodriguez | |
| 2010/0068629 A1* | 3/2010 | Gordon | 429/325 |
| 2010/0087885 A1* | 4/2010 | Atanasoska | A61N 1/378 607/9 |
| 2013/0017445 A1 | 1/2013 | Hodgkinson et al. | |

FOREIGN PATENT DOCUMENTS

WO  WO2008/052136  *  5/2008
WO  2010/040065 A1  4/2010

* cited by examiner

DEGRADABLE IMPLANTABLE BATTERY

CROSS-REFERENCE TO RELATED APPLICATIONS

This application is a continuation of U.S. patent application Ser. No. 14/077,397, filed on Nov. 12, 2013, which is a continuation in part and claims the benefit and priority of U.S. patent application Ser. No. 13/183,708, filed on Jul. 15, 2011, the entire contents of which are incorporated herein by reference.

BACKGROUND

The present disclosure relates to biodegradable implantable batteries and methods for preparing the same.

Various types of medical devices are designed to be implanted within the human body. Examples include stents, scaffolds, drug delivery devices, cardiac rhythm management devices, neurological stimulation devices, and the like. As electronics, sensors, pacemakers, and cameras are miniaturized it is becoming feasible to deploy smaller devices into the body.

Some implantable medical devices are designed to function by utilizing energy from a power source. Such devices often require an on-board power source, which is implanted into the body as part of the medical device and is housed within a sealed case. In many circumstances, the sealed case is made from a noble metal, such as titanium, to prevent exposure of the contents of the battery to the in vivo environment. This serves to protect the battery from degradation and the patient from toxic byproducts if the battery leaks, or if the battery is left in the body either inadvertently or during long-term applications.

In the absence of recharging, batteries can only provide a finite amount of power before they are discharged to the point of being useless. In circumstances where a battery has been completely discharged, the battery and the associated medical device must generally be explanted and replaced by a new one, unless the battery was only intended for temporary use. For example, when the battery inside a pacemaker no longer provides sufficient power, the pacemaker must generally be surgically removed and replaced with a new pacemaker.

Unfortunately, removal of implanted devices is not always an easy task. The body's immunological response to a foreign body generally results in the formation of fibrous tissue around an implanted medical device over time. This fibrous tissue can make it difficult to remove implanted medical devices without risking harm to the patient. Accordingly, implantable batteries that overcome the shortcomings of prior art power sources remain desirable.

SUMMARY

The present disclosure provides a biodegradable battery including an anode comprising a material including an inner surface and an outer surface, wherein electrochemical oxidation of the anode material results in the formation of a reaction product that is substantially non-toxic and a cathode comprising a material including an inner surface and an outer surface, the inner surface of the cathode being separated from the inner surface of the anode by a permeable membrane in direct fluid contact with the aqueous environment in the body; wherein electrochemical reduction of the cathode material results in the formation of a reaction product that is substantially non-toxic, and wherein the cathode material presents a larger standard reduction potential than the anode material.

The present disclosure provides for a biodegradable battery according to another embodiment of the present disclosure. The battery includes an anode comprising a material including an inner surface and an outer surface, wherein electrochemical oxidation of the anode material results in the formation of a reaction product that is substantially non-toxic; a cathode comprising a cathode including an inner surface and an outer surface, the inner surface of the cathode being separated from the inner surface of the anode by a permeable membrane in direct fluid contact with the aqueous environment in the body; and a biodegradable coating disposed over the outer surface of the cathode and a portion of the outer surface of the anode, wherein electrochemical reduction of the cathode material results in the formation of a reaction product that is substantially non-toxic, and wherein the cathode material having a larger standard reduction potential than the anode material.

The present disclosure provides for a biodegradable battery according to a further embodiment of the present disclosure. The battery includes an anode comprising a material including an inner surface and an outer surface, wherein electrochemical oxidation of the anode material results in the formation of a reaction products that is substantially non-toxic; a cathode comprising a material, including an inner surface and an outer surface, the inner surface of the cathode being separated from the inner surface of the anode by a permeable membrane in direct fluid contact with the aqueous environment in the body; a biodegradable coating disposed over the outer surface of the cathode and only a portion of the outer surface of the anode; and a hydrogel layer disposed over the outer surface of the anode, the hydrogel layer including at least one precursor material, wherein electrochemical reduction of the cathode material results in the formation of a reaction product that is substantially non-toxic, and wherein the cathode material having a larger standard reduction potential than the anode material.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1B:
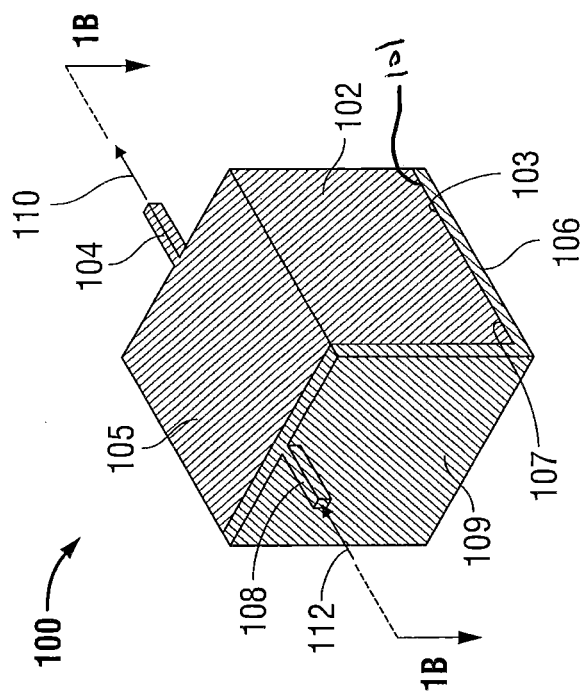
FIG. 1B is a cross-sectional view of the battery of FIG. 1A taken along the line 1B-1B in FIG. 1A.

The present disclosure provides an implantable battery including an anode, a cathode and an optional biodegradable coating. As used herein, the term "biodegradable" in reference to a material shall refer to the property of the material being able to be harmlessly absorbed by the body. In the present application, the terms "biodegradable," "bioresorbable," and "bioabsorbable" are used interchangeably and are intended to mean the characteristic according to which a material decomposes, or loses structural integrity under body conditions (e.g., enzymatic degradation or hydrolysis) or are broken down (physically or chemically) under physiologic conditions in the body such that the degradation products are excretable or absorbable by the body after a given period of time. The time period may vary, from about one hour to about several months or more, depending on the chemical nature of the material. In embodiments, the material may not be completely absorbed, provided the non-absorbed material poses no health risks and is biocompatible.

The anode and the cathode utilized in forming the implantable battery of the present disclosure include two or more materials having dissimilar electrochemical potentials, with the anode and the cathode being separated by a permeable membrane in direct fluid contact with the aqueous environment in the body. The anode includes an oxidizable material that generates electrons and the cathode includes a reducible material that accepts electrons, the cathode material having a larger standard reduction potential than the anode material. Electrochemical oxidation of the anode material and reduction then final degradation of the cathode material results in the formation of reaction products that are substantially non-toxic. As used herein the term "substantially non-toxic" in reference to a chemical compound shall refer to the property of the chemical compound being unlikely to cause harm to an individual at dosages that are reasonably foreseeable given the manner in which the chemical compound is being used and/or produced.

Due to the mismatch in potentials, an electrochemical cell between the anode and the cathode is established in which the material possessing a more negative electrochemical potential (e.g., the anode) degrades while the other material (e.g., the cathode) remains intact due to cathodic protection. As current passes from the anode to the cathode, the anode material degrades due to galvanic corrosion. The corrosion produces the flow of electrons from the anode to the cathode as the anode reacts with water and other substances present at the implantation site (e.g., in vivo environment). The positive net flow of electrons at the cathode elevates its potential, thereby protecting the cathode from degradation in an otherwise corrosive environment. Thus, as the anode and the cathode form an electrochemical cell, the anode continuously degrades providing for the electron flow, while the cathode is cathodically protected, thereby generating current.

The battery according to the present disclosure may generate a voltage potential from about 0.01 volts (V) to about 2.5 V, in embodiments from about 0.01 V to about 1.0 V, and may have a capacity of from about 0.058 milliampers per hour per $cm^2$ ($mAh/cm^2$) to about 66.5 $mAh/cm^2$, in embodiments from about 1 mAh to about 40 mAh. Once the anode has completely degraded, the current generation ceases and the cathode is no longer cathodically protected, resulting in subsequent degradation of the cathode material and the battery.

The amount of the anode material may be from about 40% to about 99%, from about 90% to about 99%, in further embodiments from about 95% to about 99% by weight of the combined mass of the anode and the cathode. The amount of the cathode material may be from about 1% to about 60%, in embodiments from about 1% to about 10%, in further embodiments from about 1% to about 5% by weight of the combined mass of the anode and the cathode.

The anode can be made of various metals, various alloys of metals, compounds including metal atoms, ceramic/metal composites, various polymers, and combinations thereof. Suitable metals and alloys for forming the anode include, but are not limited to, calcium, magnesium, iron, bismuth, zinc, electrochemically oxidizable degradable polymers such as organometallic polymers, their alloys, and combinations of any of the foregoing. Additional first materials may include polypyrrole based positive electrode arrays, carbon microelectromechanical systems, iron oxide carbon nanofibers, lithium based anodes such as lithium titanium phosphate, metal oxides such as zinc oxide with conductive ceramics such as magnesium hydroxide and calcium hydroxide, nanocomposites, cobalt iron oxides, combinations thereof, and the like.

The cathode may include materials including, but not limited to, metal oxides, metal hydroxides, metal oxyhydroxides, polyoxymetallates, metal salts, electrochemically reducible organic compounds, electrochemically reducible bioresorbable polymers, and combinations thereof. Suitable metal oxides include, but are not limited to, manganese oxides (e.g., $Mn_2O_3$ and $MnO_2$) iron(III) oxide, bismuth oxides (e.g., $Bi_2O_3$ and $Bi_2O_4$) and combinations thereof. Suitable metal oxyhydroxides include, but are not limited to, manganese oxyhydroxide. Suitable metal salts include, but are not limited to, metal halides such as iron chloride, metal sulfides such as iron sulfide and bismuth sulfide, metal sulfates such as iron sulfate and manganese sulfate, metal phosphates such as iron phosphate and manganese phosphate, and combinations thereof.

Suitable electrochemically reducible organic compounds for use as a cathode include, but are not limited to, electrochemically active biological compounds, including metalloenzymes and metalloproteins, such as ferredoxins, oxidases (e.g., cytochrome c oxidase), peroxidases, catalases, superoxide dismutases, metal ion containing macrocycle compounds, such as porphyrins, phthalocyanines, tetraazamacrocycles, and combinations thereof.

Suitable electrochemically reducible bioresorbable polymers include, but are not limited to, non-toxic conjugated or nonconjugated polymeric disulfide compounds, conjugated or nonconjugated metallopolymers based on nontoxic metal ion complexes, such as ferrocene (including polyvinylferrocene), Schiff bases or heterocycle metal ion complexes, such as porphyrins, phthalocyanines, tetraazamacrocycles, and combinations thereof. Suitable electrochemically reducible bioresorbable polymers also include conjugated organic polymers such as polypyrroles, polythiophenes, polyanilines, polyethylene oxide, polylactide, polycaprolactone, and combinations thereof. Other cathode materials include, but are not limited to, sodium iron oxide, potassium iron manganese oxide, calcium zincate, zinc manganese oxide, Birnessite type manganese oxide, iron-manganese phosphate composites, sodium or potassium cobalt manganese calcium oxide, olivine, spherical spinels, spinels, polypyrrole, maghemite, and combinations thereof. In embodiments, the cathode may be a dual active material composite cathode formed from sulfur and oxide.

Exemplary pairings of anode and cathode materials include, but are not limited to, those described in Table 1 below.

TABLE 1

| Anode material | Cathode material |
| --- | --- |
| Mg | MnOOH |
| Mg | $FePO_4$ |
| Mg | Ferredoxin |
| Mg | Polyethylenedisulfide |
| Fe | FeOOH |

The battery may also include a biodegradable coating disposed about the battery, which may be formed from any suitable biodegradable polymer. The coating covers a majority of the exposed surface of the cathode and may include one or more apertures therein to provide for a fluid exchange with the anode and permeable membrane between the cathode and anode. In embodiments, the coating may also expose the cathode to the body fluids to maintain charge balance and provide for current flow. Thus, the coating exposes only the anode to the corrosive environment while encasing the cathode. The coating may be degradable at a predetermined rate and/or only at desired surfaces. In embodiments, the coating may be of varying thicknesses across different surfaces of the battery.

Suitable biodegradable polymers which may be used to form a coating of a battery of the present disclosure include polymers such as aliphatic polyesters; polyamides; polyamines; polyalkylene oxalates; poly(anhydrides); polyamidoesters; copoly(ether-esters); poly(carbonates) including tyrosine derived carbonates; poly(hydroxyalkanoates) such as poly(hydroxybutyric acid); poly(hydroxyvaleric acid); and poly(hydroxybutyrate); polyimide carbonates; poly(imino carbonates) such as poly (bisphenol A-iminocarbonate and the like); polyorthoesters; polyoxaesters including those containing amine groups; polyphosphazenes; poly (propylene fumarates); polyurethanes; polymer drugs such as polydiflunisol; polyaspirin; and protein therapeutics; biologically modified (e.g., protein; peptide) bioabsorbable polymers; and combinations thereof.

More specifically, for the purpose of this disclosure, aliphatic polyesters which may be utilized include, but are not limited to, homopolymers and copolymers of lactide (including lactic acid, D-L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, Δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, α,α diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one, and combinations thereof.

Other suitable biodegradable polymers include, but are not limited to, poly(amino acids) including proteins such as collagen (I, II and III), elastin, fibrin, fibrinogen, silk, and albumin, peptides including sequences for laminin and fibronectin (especially its RGD site), polysaccharides such as hyaluronic acid (HA), dextran, alginate, chitin, chitosan, and cellulose, glycosaminoglycan, gut, and combinations thereof. Collagen as used herein includes natural collagen such as animal derived collagen, gelatinized collagen, or synthetic collagen such as human or bacterial recombinant collagen.

Additionally, synthetically modified natural polymers such as cellulose and polysaccharide derivatives, including alkyl celluloses, hydroxyalkyl celluloses, cellulose ethers, cellulose esters, nitrocelluloses, and chitosan may be utilized as coating of a battery of the present disclosure. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose (CMC), cellulose triacetate, cellulose sulfate sodium salt, and combinations thereof. These may be collectively referred to herein, in embodiments, as "celluloses."

In embodiments, the coating may be a hydrogel disposed on the surface of the anode, thereby providing for a controlled exposure of the anode to the fluids present in vivo. This slows the degradation rate of the anode and prolongs the longevity of the battery. Suitable hydrogels are within the purview of those skilled in the art and include, for example, those discussed in U.S. Pat. Nos. 6,184,266, 6,368,356, and 7,605,232, the entire disclosures of each of which are incorporated by reference herein.

The coating may be present in an amount from about 500 nm to about 2 mm, in embodiments from about 1 μm to about 500 μm in thickness. Thicker and thinner coatings may also be possible. Denser, more water impermeable coatings may be thinner, while porous, more water permeable coatings may be thicker to cause slowing of degradation rate. Battery longevity may be controlled by adjusting the degradation rate and the mass of the anode. Current delivered by the battery depends on the degradation rate of the anode which, in turn, depends on the surface area exposed to the corrosive in vivo environment. In embodiments, the surface area of the battery may also be adjusted by modifying the shape of the anode and the cathode, and/or providing a coating, to tailor the exposed surface to achieve a desired degradation rate.

Figure 1A:
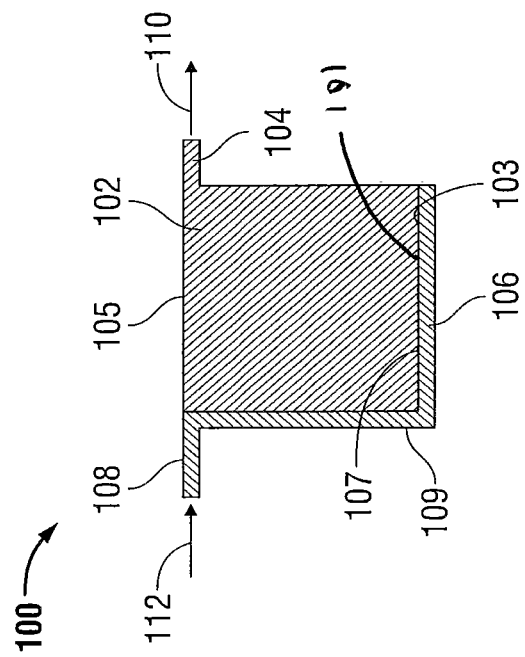
FIG. 1A is a perspective view of a battery according to the present disclosure.

Referring now to FIGS. 1A and 1B, perspective and cross-sectional views of a battery assembly 100, respectively. The battery assembly 100 includes an anode 102, and a cathode 106. A permeable membrane 101 is disposed between the anode and cathode. The anode 102 has a substantially rectangular cross-sectional shape and the cathode 106 is disposed as a relatively thin layer on the surface of the anode 102.

During operation, an electrochemical oxidation reaction takes place at the anode 102 liberating electrons that can then be used to drive a load (e.g., a medical device). The anode material can be selected so that the reaction products of the electrochemical oxidation are substantially non-toxic. In this manner, the reaction products at the anode can simply be absorbed by the body.

The cathode 106 may also be formed from a material that when electrochemically reduced forms products that are substantially non-toxic. Cathode materials disclosed herein may be selected so that the cathode material has a higher oxidation potential than the material of the anode. In other words, the cathode material may be selected so that is has a larger standard reduction potential than the material of the anode.

In embodiments, the cathode material may be a material configured to intercalate or otherwise capture ions produced during electrochemical oxidation of the anode, such that if electrochemical oxidation of the anode material results in the formation of metal (e.g., magnesium) ions, the cathode material can be selected to be a material that can intercalate metal ions. In further embodiments, the cathode material may be a material configured to intercalate ions other than those produces by the anode 102, such as sodium and/or hydrogen ions.

The anode 102 is described as being composed of magnesium and the cathode 106 being composed of manganese (IV) oxide. Without being bound by any particular theory, when the magnesium is electrochemically oxidized, magnesium ions are formed and then absorbed into the body. Magnesium is a required nutrient and as such is substantially non-toxic at the concentrations that would likely be achieved by embodiments as disclosed herein. When the manganese (IV) oxide is electrochemically reduced, manganese (III) oxide is formed, which may be further reduced to manganese (II) hydroxide and then absorbed by the body.

As shown in FIGS. 1A and 1B, the anode 102 is in physical and/or electrochemical contact with the cathode 106. In embodiments, the battery 100 may include a plurality of cells including a plurality of anodes 102 and cathodes 106. The anode 102 includes an inner surface 103. The anode 102 and the cathode 106 also include outer surfaces 105 and 109, respectively. As used herein, the term "inner surface" denotes surfaces of the anode 102 and the cathode 106 that are facing each other, whereas the term "outer surface" denotes outward surfaces facing the in vivo environment. The outer surfaces 105 and 109 are exposed to the in vivo environment aiding in the degradation of the anode 102 and the cathode 106 and the battery 100. The anode 102 also includes a first conductor 104 and the cathode 106 includes a second conductor 108. Each of the conductors 104 and 108 is coupled to a load (not shown).

The current generated between the anode 102 and the cathode 106 may be used to power any number of implantable devices. The load may be any temporary or permanently implanted medical device that utilizes a power source and may include both biosorbable and non-biosorbable medical devices. Exemplary medical devices may include, but are not limited to, neurological stimulators, implantable sensors, implantable cardiac rhythm management devices, such as pacemakers, cardiac resynchronization therapy (CRT) devices, remodeling control therapy (RCT) device, cardioverter/defibrillators, or pacemaker-cardioverter/defibrillators, and the like.

When the battery 100 is activated, a current is generated and is delivered to the load through the conductors 104 and 108. Specifically, electrons flow from the anode 102 in the direction of arrow 110 through the first conductor 104. The electrons can then pass through the load, through the second conductor 108 in the direction of arrow 112, before completing the circuit at the cathode 106. In order to maintain charge balance, positively charged ions move from the anode 102 to the cathode 106.

During the discharging process, the anode 102 dissolves as the anode material is electrochemically oxidized. In embodiments where the anode material is magnesium, the anode 102 is broken down according to the following reaction represented by formula (I):

$$Mg \rightarrow Mg_2^+ + 2e^-  \quad (I)$$

In embodiments where the cathode 106 is manganese (IV) oxide, the corresponding half-cell reaction at the cathode is described by the following half-cell reaction represented by formula (II):

$$2MnO_2 + H_2O + 2e^- \rightarrow Mn_2O_3 + 2OH^- \quad (II)$$

As the anode 102 reacts, a soluble species (e.g., $Mg^{2+}$) is formed at the anode 102 which dissolves into the extracellular fluid of the body. As described above, the cathode 106 is cathodically protected from degradation. After the anode 102 is completely degraded, the cathode 106 is no longer cathodically protected and degrades as follows: manganese (III) oxide forms at the cathode 106, which can be further reduced to manganese (II) hydroxide and then dissolves in the extracellular fluid of the body. As such, the anode 102 and cathode 106 erode and are completely dissolved, resulting in degradation of the battery 100.

In embodiments, electrochemical reduction at the cathode 106 forms a chemical species that, while not highly soluble in the aqueous in vivo environment, nonetheless subsequently breaks down chemically and dissolves after the battery 100 is no longer operational. As such, even in these circumstances, the components of the battery are absorbed by the body.

Figure 2B:
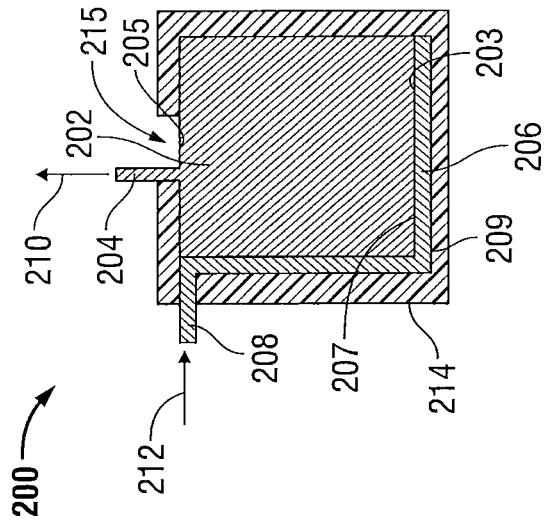
FIG. 2B is a cross-sectional view of the battery of FIG. 2A taken along the line 2B-2B in FIG. 2A.
Figure 2A:
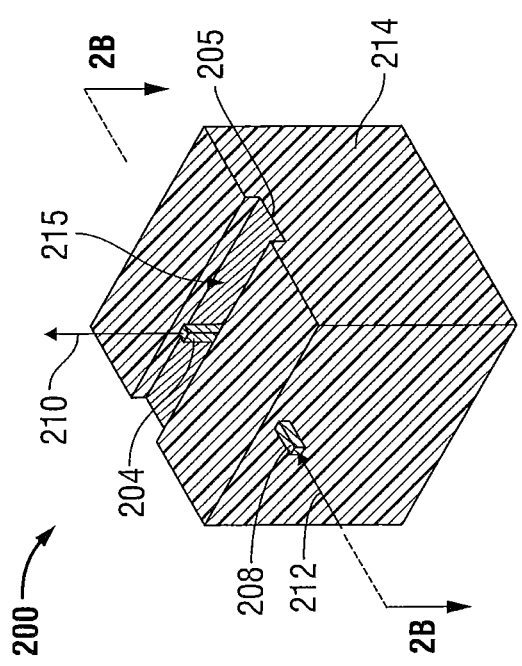
FIG. 2A is a perspective view of another battery according to the present disclosure.

FIGS. 2A and 2B, show perspective and cross-sectional views of an alternate battery 200, respectively. The battery 200 includes an anode 202 and a cathode 206. The anode 202 is in physical and/or electrochemical contact with the cathode 206. The anode 202 includes an inner surface 203. The anode 202 and the cathode 206 also include outer surfaces 205 and 209, respectively. The anode 202 also includes a first conductor 204 and the cathode 206 includes a second conductor 208. Each of the conductors 204 and 208 is coupled to the load. Current flows from the anode 202 in the direction of arrow 210 through the first conductor 204. The current then passes through the load, through the second conductor 208 in the direction of arrow 212, before completing the circuit at the cathode 206.

The battery 200 also includes a biodegradable coating 214 disposed over the entire outer surface 209 of the cathode 206 and a portion of the outer surface 205 of the anode 202. The coating 214 includes one or more openings 216 exposing a portion of the anode 202 to the in vivo environment. This arrangement protects the cathode 206 from degradation and exposes only the anode 202 and in embodiments, the cathode 206, to the corrosive environment. The coating 214 may be degradable at a predetermined rate. The coating 214 may fully degrade from about 2 hours to about 2 yrs, in embodiments from about 2 hours to about 1 yr.

In embodiments, the coating 214 does not completely degrade faster than the anode 202. Alternatively, the coating 214 could last only until the battery 200 is activated. In further embodiments, a series of batteries 200 may be implanted, each with a coating 214 having a different degradation time so as to extend the time over which a device is powered. In this embodiment, each battery 200 in the series would activate as the proceeding battery is exhausted. For a device requiring very low power and a slow degrading battery the activation time could be from a few hours for the first battery 200 to several months or more for the last battery 200 to be activated.

The coating 214 may degrade at different rates on different portions of the outer surfaces 205 and 209. In embodiments, the portion of the coating 214 covering the outer surface 209 of the cathode 206 may degrade at a slower rate than the portion of the coating 214 covering the outer surface 205 of the anode 202, allowing the anode 202 to be degraded prior to the cathode 206 being exposed to the in vivo environment. This may be accomplished by adjusting the thickness of the coating 214 and/or the chemical constituents thereof within various portions thereof.

Figure 3B:
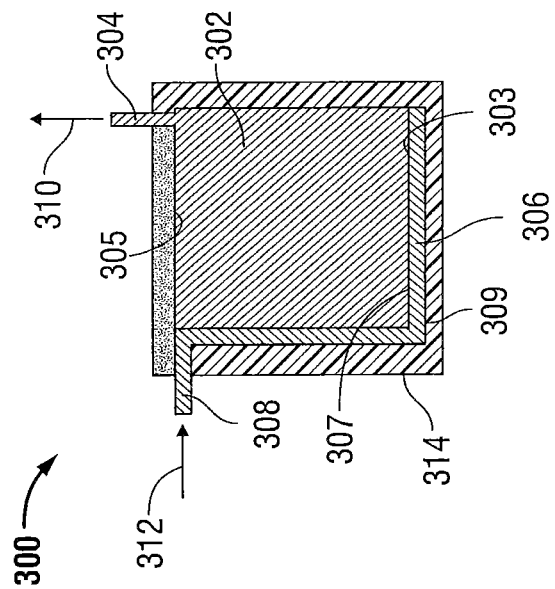
FIG. 3B is a cross-sectional view of the battery of FIG. 3A taken along the line 3B-3B in FIG. 3A.
Figure 3A:
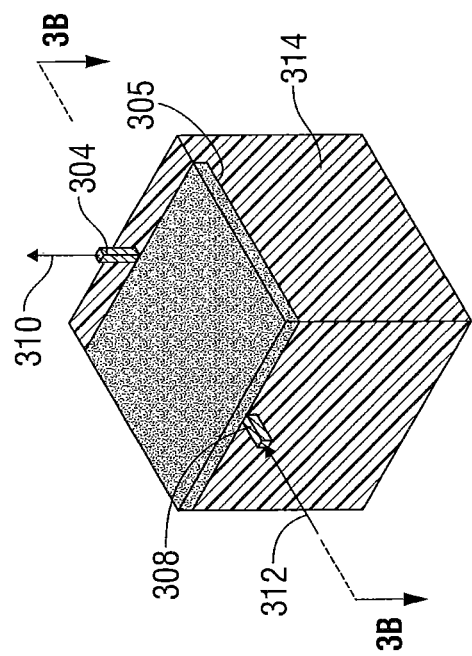
FIG. 3A is a perspective view of another embodiment of a battery according to the present disclosure.

FIGS. 3A and 3B show perspective and cross-sectional views of yet another alternate battery 300, respectively. The battery 300 includes an anode 302 and a cathode 306. The anode 302 is separated from the cathode 306 by a membrane such as membrane 101. The anode 302 includes an inner surface 303 separated from an inner surface 307 of the cathode 306. The anode 302 and the cathode 306 also include outer surfaces 305 and 309, respectively. The anode 302 also includes a first conductor 304 and the cathode 306 includes a second conductor 308. Each of the conductors 304 and 308 is coupled to the load. Current flows from the anode 302 in the direction of arrow 210 through the first conductor 304. The current then passes through the load, through the second conductor 308 in the direction of arrow 312, before completing the circuit at the cathode 306.

The battery 300 also includes a biodegradable coating 314 disposed over the entire outer surface 309 of the cathode 306. As shown, the coating 314 only covers the cathode 306. In embodiments, the coating 314 may also cover a portion of the outer surface 305 of the anode 302. The coating 314 is similar to the coating 214, including similar degradation properties, and it may be composed of similar constituents.

In embodiments, the battery 300 may further include a coating layer 316 disposed over the outer surface 305 of the anode 302. The coating layer 316 may be any material described above that is water-permeable or may be a water-permeable hydrogel, providing for a controlled exposure of the anode 302 to the fluids present in vivo, thereby controlling the degradation rate of the anode 302 and prolonging the longevity of the battery 300.

Figure 4B:
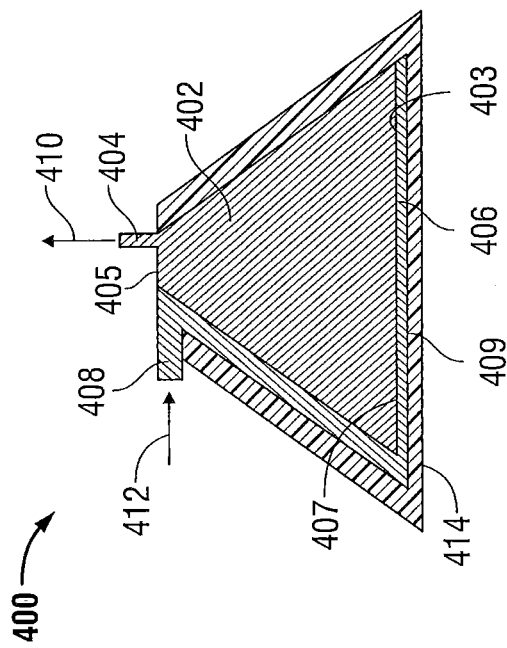
FIG. 4B is a cross-sectional view of the battery of FIG. 4A taken along the line 4B-4B in FIG. 4A.
Figure 4A:
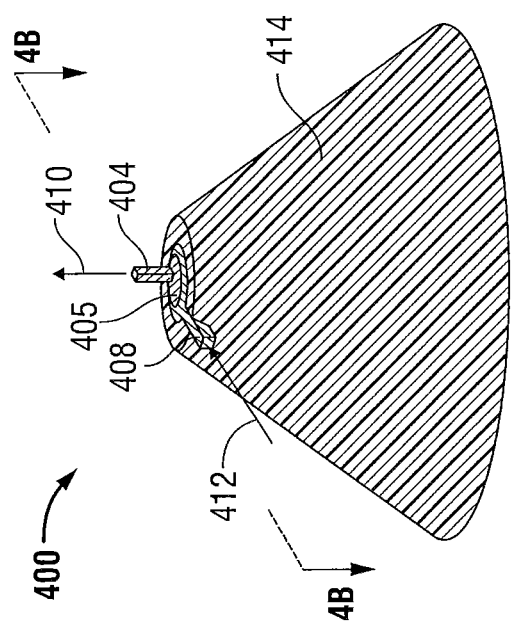
FIG. 4A is a perspective view of another embodiment of a battery according to the present disclosure.

FIGS. 4A and 4B, show perspective and cross-sectional views of another battery assembly 400, respectively. The battery 400 includes an anode 402 and a cathode 406. The anode 402 has a substantially frustoconical cross-sectional shape with the cathode 406 being disposed as a foil layer on an inner surface 403 of the anode 402. The anode 402 is separated from the cathode 406 by a membrane such as membrane 101. The anode 402 includes an inner surface 403. The anode 402 and the cathode 406 also include outer surfaces 405 and 409, respectively. The anode 402 also includes a first conductor 404 and the cathode 406 includes a second conductor 408. Each of the conductors 404 and 408 is coupled to the load. Current flows from the anode 402 in the direction of arrow 410 through the first conductor 404. The current then passes through the load, through the second conductor 408 in the direction of arrow 412, before completing the circuit at the cathode 406.

The battery 400 also includes a biodegradable coating 414 disposed over the entire outer surface 409 of the cathode 406. As shown the coating 414 only covers the cathode 406. In embodiments, the coating 414 may also cover a portion of the outer surface 405 of the anode 402. The coating 414 is substantially similar to the coating 214 including similar degradation properties and may be composed of similar constituents. The frustoconical shape of the battery 400 minimizes the surface area of the outer surface 405 of the anode 402. The dimensions (e.g., angle) of the sides of the battery 400 may be tailored to obtain a desired exposure of the anode 402 to the in vivo environment and thereby control the degradation rate thereof. The conical or frustoconical shape provides for a greater surface area of the anode 402 to be exposed as it degrades, thus impacting current supply as a function of implant time.

It will be appreciated that, in some embodiments, the tissue of the body itself can be utilized for the purpose of transferring ions between the anode and the cathode. For example, the extracellular fluid in vivo is an aqueous solution that includes at least some amount of electrolytes such as sodium and potassium. Therefore, extracellular fluid can be used to transfer ions between the anode and the cathode in embodiments. It is the expectation that in vivo fluids will transfer ions between the cathode and anode, but other means can be used.

It will be appreciated that the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, or material.

What is claimed is:

1. A biodegradable battery comprising:
    an anode comprising a material including an inner surface and an outer surface, wherein electrochemical oxidation of the anode material results in the formation of a reaction product that is substantially non-toxic; and
    a cathode comprising a material including an inner surface and an outer surface, the inner surface of the cathode being separate from the inner surface of the anode,
    wherein electrochemical reduction of the cathode material results in the formation of a reaction product that is substantially non-toxic, and wherein the cathode material presents a larger standard reduction potential than the anode material, and wherein the biodegradable battery has a substantially frustoconical shape.

2. The biodegradable battery of claim 1, wherein the anode material is selected from the group consisting of magnesium, iron, zinc, electrochemically oxidizable degradable polymers, alloys, and combinations thereof.

3. The biodegradable battery of claim 1, wherein the cathode material is selected from the group of materials consisting of metal oxides, metal hydroxides, metal oxyhydroxides, polyoxymetallates, metal salts, electrochemically reducible degradable polymers, and combinations thereof.

4. The biodegradable battery of claim 1, further comprising a biodegradable coating disposed over the outer surface of the cathode and a portion of the outer surface of the anode.

5. The biodegradable battery of claim 4, wherein the biodegradable coating comprises a polymer selected from the group consisting of aliphatic polyesters, polyamides, polyamines, polyalkylene oxalates, poly(anhydrides), polyamidoesters, copoly(ether-esters), poly(carbonates), poly(hydroxyalkanoates), poly(hydroxyvaleric acid), poly(hydroxybutyrate), polyimide carbonates, poly(imino carbonates), polyorthoesters, polyoxaesters, polyphosphazenes, poly(propylene fumarates), polyurethanes, polymer drugs, and combinations thereof.

6. The biodegradable battery of claim 1, further comprising a hydrogel layer disposed over the outer surface of the anode, the hydrogel layer comprising at least one precursor material.

7. A biodegradable battery comprising:
    an anode comprising a material including an inner surface and an outer surface, wherein electrochemical oxidation of the anode material results in the formation of a reaction product that is substantially non-toxic;
    a cathode comprising a material including an inner surface and an outer surface, the inner surface of the cathode being separate from the inner surface of the anode; and
    a biodegradable coating disposed over the outer surface of the cathode and a portion of the outer surface of the anode,
    wherein electrochemical reduction of the cathode material results in the formation of a reaction product that is substantially non-toxic, and wherein the cathode material having a larger standard reduction potential than the anode material, and wherein the biodegradable battery has a substantially frustoconical shape.

8. The biodegradable battery of claim 7, wherein the anode material comprises a material selected from the group consisting of magnesium, iron, zinc, electrochemically oxidizable degradable polymers, alloys and combinations thereof.

9. The biodegradable battery of claim 7, wherein the cathode material comprises a material selected from the group of materials consisting of metal oxides, metal hydroxides, metal oxyhydroxides, polyoxymetallates, metal salts, electrochemically reducible degradable polymers, and combinations thereof.

10. The biodegradable battery of claim 7, wherein the biodegradable coating comprises a polymer selected from the group consisting of aliphatic polyesters, polyamides, polyamines, polyalkylene oxalates, poly(anhydrides), polyamidoesters, copoly(ether-esters), poly(carbonates), poly(hydroxyalkanoates), poly(hydroxyvaleric acid), poly(hydroxybutyrate), polyimide carbonates, poly(imino carbonates), polyorthoesters, polyoxaesters, polyphosphazenes, poly(propylene fumarates), polyurethanes, polymer drugs, and combinations thereof.

11. The biodegradable battery of claim 7, further comprising a hydrogel layer disposed over the outer surface of the anode, the hydrogel layer comprising at least one precursor material.

* * * * *